US012735675B2

(12) United States Patent
Kim et al.

(10) Patent No.: US 12,735,675 B2
(45) Date of Patent: Sep. 15, 2026

(54) MICROCARRIER FOR CELL CULTURE, A METHOD FOR PRODUCING THE SAME, AND A CELL CULTURE COMPOSITION USING THE SAME

(71) Applicant: LG CHEM, LTD., Seoul (KR)

(72) Inventors: Yeji Kim, Daejeon (KR); Minchae Kim, Daejeon (KR); Jee Seon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 781 days.

(21) Appl. No.: 18/001,280

(22) PCT Filed: Sep. 6, 2021

(86) PCT No.: PCT/KR2021/011985

§ 371 (c)(1),
(2) Date: Dec. 9, 2022

(87) PCT Pub. No.: WO2022/059980

PCT Pub. Date: Mar. 24, 2022

(65) Prior Publication Data

US 2023/0250391 A1 Aug. 10, 2023

(30) Foreign Application Priority Data

Sep. 15, 2020 (KR) ........................ 10-2020-0118533
Sep. 3, 2021 (KR) ........................ 10-2021-0117811

(51) Int. Cl.
*C12N 5/00* (2006.01)
*C08F 12/08* (2006.01)

(52) U.S. Cl.
CPC ............ *C12N 5/0075* (2013.01); *C08F 12/08* (2013.01); *C12N 2531/00* (2013.01); *C12N 2533/30* (2013.01); *C12N 2535/00* (2013.01)

(58) Field of Classification Search
None
See application file for complete search history.

(56) References Cited

U.S. PATENT DOCUMENTS 4,994,388 A 2/1991 Hillegas et al.
5,013,626 A 5/1991 Matsumura et al.
5,863,957 A 1/1999 Li et al.
7,122,582 B2 10/2006 Konishi et al.
7,129,082 B2 10/2006 Van Der Merwe et al.
8,652,734 B2 2/2014 Cardoso et al.
9,115,238 B2 8/2015 Deseayes et al.
9,222,000 B2 12/2015 Frutos et al.
9,873,786 B2 1/2018 Henry et al.
10,611,924 B2 4/2020 Frutos et al.
10,941,312 B2 3/2021 Frutos et al.
11,065,593 B2 7/2021 Goldstein et al.
11,193,107 B2 12/2021 Takahashi et al.
2002/0155594 A1 10/2002 Hsieh et al.
2004/0248291 A1 12/2004 Yamamoto et al.
2005/0220752 A1 10/2005 Charmot et al.
2005/0266244 A1 12/2005 Park
2005/0272890 A1 12/2005 Konishi et al.
2008/0166328 A1 7/2008 Harmon et al.
2009/0291294 A1 11/2009 Mori et al.
2010/0093053 A1 4/2010 Oh et al.
2010/0104527 A1 4/2010 Mansky et al.
2010/0304482 A1 12/2010 Deshyes et al.
2010/0317113 A1 12/2010 Deshayes et al.
2011/0014693 A1 1/2011 Oh et al.
2011/0111498 A1 5/2011 Oh et al.
2011/0129919 A1 6/2011 Oh et al.
2011/0143433 A1 6/2011 Oh et al.
2011/0294210 A1 12/2011 Oh et al.
2012/0028352 A1 2/2012 Oh et al.
2012/0052579 A1 3/2012 Shannon et al.
2012/0219531 A1 8/2012 Oh et al.
2012/0309053 A1 12/2012 Wellings
2014/0193903 A1 7/2014 Oh et al.
2014/0315300 A1 10/2014 Oh et al.
2016/0083690 A1 3/2016 Birch et al.
2016/0145567 A1 5/2016 Henry et al.
2016/0145600 A1 5/2016 Caracci et al.
2017/0081638 A1 3/2017 Ma
2018/0201898 A1 7/2018 Takahashi et al.
2019/0112572 A1 4/2019 Figueroa et al.
2019/0144820 A1 5/2019 Oh et al.
(Continued)

FOREIGN PATENT DOCUMENTS

CA 2 886 190 A1 9/2016
CN 1903890 A 1/2007
(Continued)

OTHER PUBLICATIONS

Lerman et al. "The Evolution of Polystyrene as a Cell Culture Material" (2018) Tissue Engineering: Part B, vol. 24, No. 5: 359-372. (Year: 2018).*

Gutsche et al., "N-Acetylglucosamine and Adenosine Derivatized Surfaces for Cell Culture: 3T3 Fibroblast and Chicken Hepatocyte Response," Biotechnology and Bioengineering, vol. 43, pp. 801-809 (1994).

"Corning polystyrene microcarrier 500 g Synthemax II treated," https://www.ddbiolab.com/article/004623?language=en, accessed Jun. 29, 2024, 1 page.

Huang, et al., "Synthesis and Characterization of Crosslinked Porous Poly (styrene-co-divinylbenzene) Microspheres with Tunable Particle and Pore Diameters", Chinese Journal of Applied Chemistry, (2016) vol. 33, Iss. 4, pp. 406-411, with English Abstract, 6 pages.

Poinescu I.C. et al., "Styrene Divinylbenzene Copolymers", Die Angewandte Makromolekulare Chemie, 1998, vol. 164, pp. 45-58 (Nr. 2659).

(Continued)

*Primary Examiner* — Teresa E Knight
(74) *Attorney, Agent, or Firm* — ROTHWELL, FIGG, ERNST & MANBECK, P.C.

(57) ABSTRACT

The present disclosure relates to a microcarrier for cell culture comprising: polystyrene-based particles containing at least one or more of hydrocarbon oil having 12 or more carbon atoms, or pores derived therefrom, a method for producing the same, and a cell culture composition using the same.

19 Claims, 2 Drawing Sheets

(56) References Cited

U.S. PATENT DOCUMENTS

| | | | |
|---|---|---|---|
| 2020/0030786 | A1 | 1/2020 | Raymond |
| 2020/0032122 | A1 | 1/2020 | Nishiumi |
| 2021/0179576 | A1 | 6/2021 | Michaud et al. |
| 2022/0081684 | A1 | 3/2022 | Kim et al. |
| 2022/0186178 | A1 | 6/2022 | Henry et al. |
| 2023/0250391 | A1 | 8/2023 | Kim et al. |

FOREIGN PATENT DOCUMENTS

| | | | |
|---|---|---|---|
| CN | 101880348 | A | 11/2010 |
| CN | 102327761 | A | 1/2012 |
| CN | 104558350 | A | 4/2015 |
| CN | 106226279 | B | 11/2019 |
| CN | 106938861 | B | 7/2020 |
| EP | 4177281 | A1 | 5/2023 |
| JP | H02-016972 | A | 1/1990 |
| JP | H10-501173 | A | 2/1998 |
| JP | 2002-518570 | A | 6/2002 |
| JP | 2002-306155 | A | 10/2002 |
| JP | 2004-236553 | A | 8/2004 |
| JP | 2004-313008 | A | 11/2004 |
| JP | 2006-136212 | A | 6/2006 |
| JP | 2007-124985 | A | 5/2007 |
| JP | 2007-197471 | A | 8/2007 |
| JP | 2007-275056 | A | 10/2007 |
| JP | 2008-074979 | A | 4/2008 |
| JP | 2010-508851 | A | 3/2010 |
| JP | 2011-514169 | A | 5/2011 |
| JP | 4979946 | B2 | 7/2012 |
| JP | 2012-527901 | A | 11/2012 |
| JP | 2012-242827 | A | 12/2012 |
| JP | 2013-504669 | A | 2/2013 |
| JP | 2016-521124 | A | 7/2016 |
| JP | 6200621 | B2 | 9/2017 |
| JP | 2019-510499 | A | 4/2019 |
| JP | 6528508 | B | 6/2019 |
| JP | 2020-039356 | A | 3/2020 |
| KR | 10-2001-0053046 | A | 6/2001 |
| KR | 10-0479218 | B1 | 3/2005 |
| KR | 10-0803836 | B1 | 2/2008 |
| KR | 10-0842378 | B | 7/2008 |
| KR | 10-0871652 | B1 | 12/2008 |
| KR | 10-2009-0128287 | A | 12/2009 |
| KR | 10-2014-0008383 | A | 1/2014 |
| KR | 10-2014-0056014 | A | 5/2014 |
| KR | 10-1545217 | B1 | 8/2015 |
| KR | 10-2016-0067474 | A | 6/2016 |
| KR | 10-2017-0114993 | A | 10/2017 |
| KR | 10-2017-0121469 | A | 11/2017 |
| KR | 10-2018-0049013 | A | 5/2018 |
| KR | 10-2019-0138780 | A | 12/2019 |
| KR | 10-2021-0011340 | A | 2/2021 |
| WO | 2015-139462 | A1 | 9/2015 |
| WO | 2019-229384 | A1 | 12/2019 |

OTHER PUBLICATIONS

Zuidema H: "Ring Method for the Determination of Interfacial Tension", Industrial and Engineering Chemistry, May 1, 1941, vol. 13, No. 5, pp. 312-313.

Extended European Search Report dated Jun. 26, 2023, of the corresponding European Patent Application No. 21869637.5, 14 pages.

Supplementary European Search Report for EP 21869602.9 mailed Oct. 17, 2024, 8 pages.

Costa et al., "Highly Magnetizable Crosslinked Chloromethylated Polystyrene-Based Nanocomposite Beads for Selective Molecular Separation of 4-Aminobenzoic Acid", ACS Omega, Apr. 2019, pp. 5640-5649.

PCT Search Report & Written Opinion of PCT/KR2021/011985 dated Dec. 31, 2021, 11 pages.

PCT Search Report & Written Opinion of PCT/KR2021/012358 dated Dec. 28, 2021, 14 pages.

PCT Search Report & Written Opinion of PCT/KR2020/009642 dated Nov. 11, 2020, 7 pages.

Hossein Tavassoli, et al. Large-scale production of stem cells utilizing microcarriers: A biomaterials engineering perspective from academic research to commercialized products, Biomaterials, vol. 181, Oct. 2018, pp. 333-346.

Extended European Search Report dated May 18, 2022, of the corresponding European Patent Application No. 20845090.8, 15 pages.

Haifei c et al. "Synthesis of porous Microparticles with aligned porosity" Advanced Functional Materials, vol. 18, Issue 2, Jan. 2008, pp. 222-228.

Galia, Monodisperse polymer beads as packing material for high-performance liquid chromotography: Effect of divinylbenzene content on the porous and chromatographic properties of poly(styrene-co-divinylbenzene) beads prepared in presence of linear polystyrene as a porogen, Journal of Polymer Science, Part A, Polymer Chemistry, (1994) vol. 32, Issue 11, pp. 2169-2175.

Wong, Libretext Biology, Axolotl Academia Publishing, 1.7: Fatty Acids (Year: 2021) 341 pages.

Rafiq et al. "Systematic microcarrier screening and agitated culture conditions improves human mesenchymal stem cell yield in bioreactors." Biotechnology journal (2016): 11, 473-486.

Nazli et al., Under the Microscope: Microcarriers, International Society cell & gene therapy, 2021, 7 pages.

Reibetanz et al., "Magnetite nanoparticles as reporters for microcarrier processing in cytoplasm." Nuclear Instruments and Methods in Physics Research B. (2011): vol. 269, Issue 2, pp. 2281-2285.

Ataman Chemicals, Dodecane, 2020, 7 pages.

Sigma Aldrich, Products: Food & cosmetics component standards: 44010, Dodecane, 2026, 11 pages.

Mindat.org, Magnetite, 2026, 20 pages.

* cited by examiner

【FIG. 1】
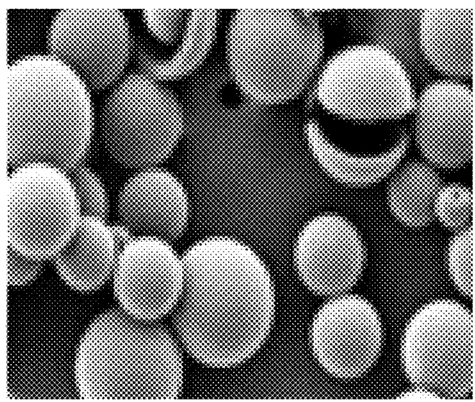
【FIG. 2】
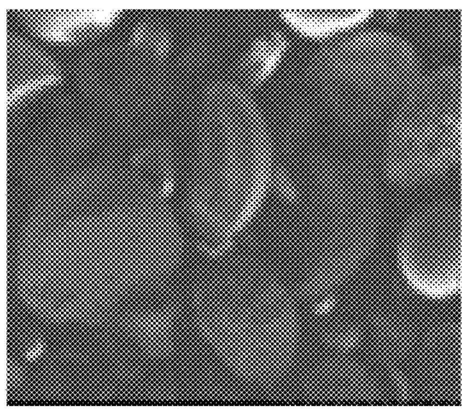
【FIG. 3】
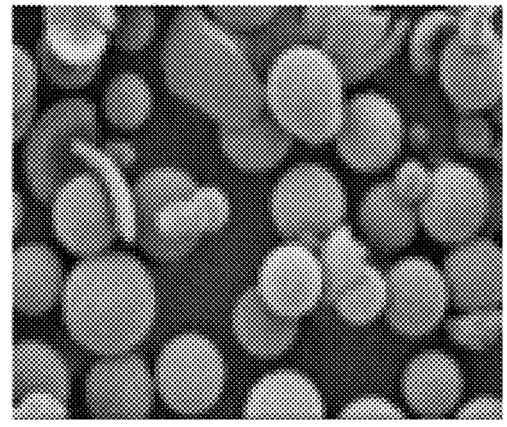

【FIG. 4】
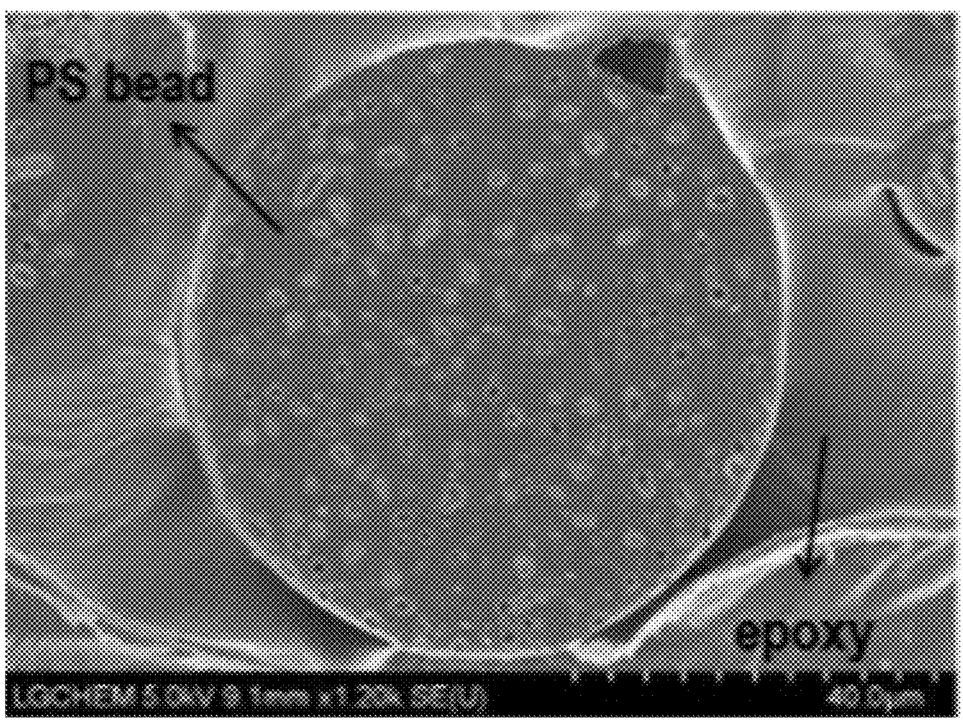
【FIG. 5】
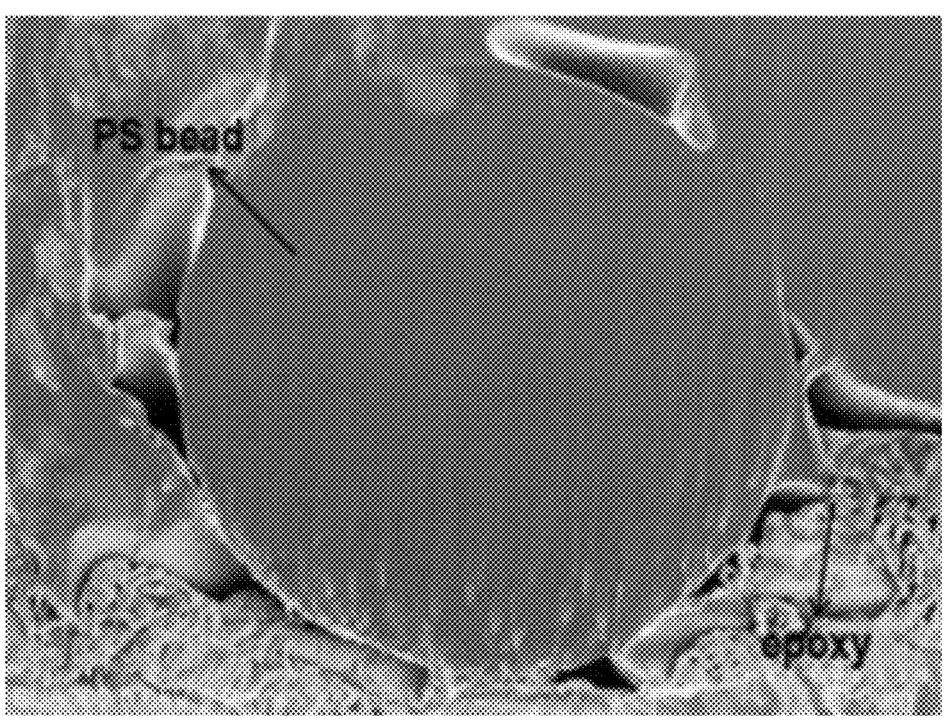

MICROCARRIER FOR CELL CULTURE, A METHOD FOR PRODUCING THE SAME, AND A CELL CULTURE COMPOSITION USING THE SAME

CROSS-REFERENCE TO RELATED APPLICATION(S)

This application is a 35 U.S.C. 371 National Phase Entry Application from PCT/KR2021/011985 filed on Sep. 6, 2021, which claims the benefits of Korean Patent Application No. 10-2020-0118533 filed on Sep. 15, 2020 and Korean Patent Application No. 10-2021-0117811 filed on Sep. 3, 2021 with the Korean Intellectual Property Office, the disclosures of which are incorporated herein by reference in their entirety.

TECHNICAL FIELD

The present disclosure relates to a microcarrier for cell culture, a method for producing the same, and a cell culture composition using the same.

BACKGROUND OF THE INVENTION

Along with the expansion of the fields of biopharmaceuticals and regenerative medicine, the need for the large-scale culture techniques capable of efficiently producing cells, tissues, microorganisms, and the like is growing.

Adherent cells are cultured using microcarriers within a 3D bioreactor. A cell, a culture medium, and a microcarrier are put in a bioreactor, and the cells are brought into contact with the microcarrier while stirring the culture medium, so that the cells are attached to the surface of the microcarrier and cultured. Since the microcarrier used at this time provides a high surface area/volume to which cells can attach and proliferate, it is suitable for large-scale culture of cells.

Currently commercially used microcarriers have a density of about 1.1 to 1.3 g/cm$^3$, and the density of cells is about 1.2 g/cm$^3$. In this case, it is advantageous to adhere cells to carriers at early stages of culturing the cells within the bioreactor, but at the time of isolating and recovering cells after culturing, a centrifugal separation is difficult, and a filtering method based on the microcarriers and cell size should be utilized. However, in this case, the filter is clogged or the process time is long, and the physical damage and contamination of cells can be easily occurred, which may cause a problem that loss of cells can occur.

In order to solve the above problems, microcarriers have been produced using the properties of materials having a density of less than 1.0 g/cm$^3$ or more than 1.3 g/cm$^3$. However, in such a case, there is a drawback that the density range of carriers that can be implemented is limited, and it is difficult to sufficiently secure the yield of microcarriers having a perfect spherical shape without damage or breakage.

Therefore, there is a need to develop a new microcarrier that can be isolated more easily at the time of isolating and recovering the microcarriers and cells after cell culture, while sufficiently securing the yield of microcarriers having a perfect spherical shape without damage and breakage.

BRIEF SUMMARY OF THE INVENTION

It is one object of the present disclosure to provide a microcarrier for cell culture that can be isolated more easily at the time of isolating and recovering the microcarriers and cells after cell culture, while sufficiently securing the yield of microcarriers having a perfect spherical shape without damage and breakage.

It is another object of the present disclosure to provide a method for producing the microcarrier for cell culture.

It is yet another object of the present disclosure to provide a cell culture composition using the microcarrier for cell culture.

In order to achieve the above object, according to one aspect, there is provided a microcarrier for cell culture comprising: polystyrene-based particles containing at least one or more of hydrocarbon oil having 12 or more carbon atoms, or pores derived therefrom.

According to another aspect, there is provided a method for producing a microcarrier for cell culture, which comprises the step of proceeding a suspension polymerization reaction of a monomer composition containing a styrene monomer in the presence of a hydrocarbon oil having 12 or more carbon atoms.

According to yet another aspect, there is provided a cell culture composition comprising a cell and the microcarrier for cell culture.

DETAILED DESCRIPTION OF THE INVENTION

Hereinafter, a microcarrier for cell culture, a method for producing the same, and a cell culture composition using the same according to specific embodiments of the present disclosure will be described in more detail.

Unless otherwise specified throughout this specification, the technical terms used herein are only for reference to specific embodiments and is not intended to limit the present disclosure.

The singular forms "a", "an", and "the" used herein include plural references unless the context clearly dictates otherwise.

The term "including" or "comprising" used herein specifies a specific feature, region, integer, step, action, element and/or component, but does not exclude the presence or addition of a different specific feature, region, integer, step, action, element, component and/or group.

The terms including ordinal numbers such as "a first", "a second", etc. are used only for the purpose of distinguishing one component from another component, and are not limited by the ordinal numbers. For instance, a first component may be referred to as a second component, or similarly, the second component may be referred to as the first component, without departing from the scope of the present disclosure.

Embodiments of the present disclosure will be described in more detail below.

1. Microcarrier for Cell Culture

According to one embodiment of the present disclosure, there can be provided a microcarrier for cell culture comprising: polystyrene-based particles containing at least one or more of hydrocarbon oil having 12 or more carbon atoms, or pores derived therefrom.

The present inventors have found through experiments that in the case of the microcarrier for cell culture of the one embodiment, at least one or more of hydrocarbon oil having 12 or more carbon atoms, or pores derived therefrom, is contained inside the polystyrene-based particles, whereby not only the density of microcarriers for cell culture can be reduced, but also the ratio of perfect spherical particles without damage or breakage is significantly increased, so that a homogeneous spherical microcarrier can be secured in high yield. The present disclosure has been completed on the basis of such findings.

Specifically, the microcarrier for cell culture may include polystyrene-based particles containing at least one or more of hydrocarbon oil having 12 or more carbon atoms, or pores derived therefrom. That is, the polystyrene-based particles may include one type of hydrocarbon oil having 12 or more carbon atoms, one type of pores derived from the hydrocarbon oil having 12 or more carbon atoms, or a mixture of these two types.

When the polystyrene-based particles contain one type of pores derived from the hydrocarbon oil having 12 or more carbon atoms, or contain both the hydrocarbon oil having 12 or more carbon atoms and the pores derived from hydrocarbon oil having 12 or more carbon atoms, the polystyrene-based particles may correspond to porous polystyrene-based particles.

The polystyrene-based particles can be produced as in the production method of another embodiment described later, in which polystyrene particles are produced by a suspension polymerization in the presence of hydrocarbon oil, so that the hydrocarbon oil continues to remain trapped inside the polystyrene particles, or part or all of the trapped hydrocarbon oil may escape by the high-speed suspension polymerization and agitation conditions, and pores may be formed inside the polystyrene particles.

The pores means an empty space inside the polystyrene-based particles, and can be used in the sense of pores, hollows, holes, voids, and the like.

The pores may be derived from the hydrocarbon oil having 12 or more carbon atoms. Specifically, the pores corresponds to a space formed by phase-separating the hydrocarbon oil having 12 or more carbon atoms from polystyrene during suspension polymerization.

Therefore, "the polystyrene-based particles contain only one type of hydrocarbon oil having 12 or more carbon atoms" means that the hydrocarbon oil is completely phase-separated in the polymerization process, but did not disappear to the outside of the particles during the polymerization and washing process. "The polystyrene-based particles contain only one type of pores derived from hydrocarbon oil having 12 or more carbon atoms" means a state in which the hydrocarbon oil is completely phase-separated in the polymerization process and disappeared to the outside of the particles during the polymerization and washing processes. Further, "the polystyrene-based particles contain both the hydrocarbon oil having 12 or more carbon atoms and the pores derived from the hydrocarbon oil having 12 or more carbon atoms" means a state in which the hydrocarbon oil is partially phase-separated and disappeared in the polymerization process and a part thereof remains.

The present inventors have found that in order to demonstrate that the pores are derived from a hydrocarbon oil having 12 or more carbon atoms, at the time of analyzing the components of the microcarrier for cell culture obtained in the one embodiment, the hydrocarbon oil having 12 or more carbon atoms is detected. Specifically, the microcarrier for cell culture obtained in the one embodiment is freeze-pulverized and dissolved in chloroform to extract unreacted residual compounds, and detailed components are qualitatively and quantitatively analyzed through GC/FID (gas chromatography-flame ionization detector). As a result, oil or a component derived therefrom was detected. Through this, it could be confirmed that hydrocarbon oil having 12 or more carbon atoms or a component derived therefrom remained inside the pores.

Specifically, the diameter of the pores may be 0.1 μm to 5 μm. More specifically, the diameter of the pores may be 0.1 μm or more, or 1 μm or more, may be 5 μm or less, or 3 μm or less, and may be 0.1 μm to 10 μm, or 0.1 μm to 5 μm, or 1 μm to 5 μm, or 1 μm to 4 μm.

As described above, as the pores are derived from hydrocarbon oil having 12 or more carbon atoms, the diameter of the pores is 0.1 μm to 5 μm and small-sized pores can be implemented, and thereby, the density of the microcarriers can be easily adjusted.

Conventionally, in order to reduce the density of the polystyrene particles, a low boiling point foaming agent was added during the polystyrene polymerization process and then formed styrene was produced through an additional foaming process. However, in such a case, a large pore having a size of several tens of μm is formed, and there is a limit that adjustment of the density of the microcarriers is difficult.

The carbon number of the hydrocarbon oil may be 12 or more, or 12 or more and 50 or less, or 12 or more and 16 or less. When the carbon number of the hydrocarbon oil is excessively reduced to less than 12, due to a decrease in the phase separation rate between hydrocarbon oil and polystyrene during suspension polymerization, there is a limitation in that the surface of particles are not uniform and a large number of recessed particles are produced.

Specifically, the hydrocarbon oil may include a linear or branched saturated hydrocarbon compound having 12 or more and 50 or less carbon atoms. The linear or branched saturated hydrocarbon compound having 12 or more and 50 or less carbon atoms may be used alone or in combination. Examples of the linear or branched saturated hydrocarbon compound having 12 or more and 50 or less carbon atoms include a normal alkane having 12 or more and 16 or less carbon atoms, an isoalkane having 12 or more and 16 or less carbon atoms, or a mixture thereof.

More specifically, as the hydrocarbon oil, dodecane having 12 carbon atoms, hexadecane having 16 carbon atoms, or Isopar M (a mixture of isoalkane having 12 to 14 carbon atoms and isoalkane having 13 to 16 carbon atoms) can be used.

The hydrocarbon oil may be contained in an amount of 30% by weight or less, or 10% by weight or more and 30% by weight or less, based on the total weight (100% by weight) of the dispersed phase composition containing a styrene monomer. Specifically, the lower limit of the content of the hydrocarbon oil is 10% by weight or more, or 11% by weight or more, or 12% by weight or more, or 13% by weight or more, or 14% by weight or more, and the upper limit thereof may be, for example, 30% by weight or less, or 25% by weight or less, or 20% by weight or less. When the content of the hydrocarbon oil is used below the content range, it is difficult to secure carrier particles with low density characteristics, and when the content range is excessively exceeded, it is difficult for the shape of the polystyrene-based particles to have a spherical shape and thus, the uniformity of the particles produced is reduced.

The density of the hydrocarbon oil may be 0.75 g/cm$^3$ or more and 0.80 g/cm$^3$ or less, or 0.75 g/cm$^3$ or more and 0.791 g/cm$^3$ or less. Since the density of the hydrocarbon oil is very low in the above-mentioned range, the density of the polystyrene-based particles can be significantly reduced accordingly.

However, when the density of the hydrocarbon oil is excessively reduced to less than 0.75 g/cm$^3$, there is a limitation in that the phase separation rate between hydrocarbon oil and polystyrene is reduced during suspension polymerization and thus the surface of the particles are not uniform, and a large number of recessed particles are produced.

Specifically, the apparent density of the polystyrene-based particles may be 0.95 g/cm$^3$ or more and less than 1.00 g/cm$^3$. As it has the above-described low density range, the cells and the microcarriers can be easily isolated through the difference in the sedimentation rate due to gravity when isolating and recovering the microcarriers and the cells after cell culture.

When the density of the microcarriers exceeds 1 g/cm$^3$, the difference in density between cells and microcarriers is small, and thus centrifugal separation may be difficult when isolating and recovering cells after culturing. When the density of the microcarrier is less than 0.95 g/cm$^3$, the microcarrier floats only on the surface of the culture medium at early stages of culture, and so it may be difficult to attach cells.

The cells are adherent animal cells, and examples thereof are not particularly limited. For example, the cells may be fibroblasts, epithelial cells, osteoblasts, chondrocytes, hepatocytes, human-derived umbilical cord blood cells, human bone marrow-derived mesenchymal stem cells, CHO (Chinese hamster ovary) cells, kidney cells (HEK293, BHK21, MDCK, vero cells, etc.), or a mixture of two or more thereof.

The density of the cells may be 1.02 g/cm$^3$ or more and less than 1.1 g/cm$^3$.

Further, a difference in density between the microcarrier for cell culture and the cells may be 0.02 g/cm$^3$ or more and 0.20 g/cm$^3$ or less. As the density difference between the cell culture microcarrier and the cell satisfies 0.02 g/cm$^3$ or more and 0.20 g/cm$^3$ or less, cells and microcarriers can be easily isolated through the difference in sedimentation rate due to gravity when isolating and recovering the microcarriers and cells after cell culture.

The polystyrene-based particles may include a polystyrene-based polymer in which at least one or more of a hydrocarbon oil having 12 or more carbon atoms, or pores derived therefrom are dispersed therein.

That is, the polystyrene-based particles may include a polystyrene-based polymer matrix in which at least one of a hydrocarbon oil having 12 or more carbon atoms dispersed in the polystyrene-based polymer matrix, or pores derived therefrom.

The polystyrene-based polymer may include a reaction product of 1 part by weight of a styrene monomer; and more than 0.033 parts by weight and less than 3 parts by weight, or 0.1 part by weight or more and 1 part by weight or less, or 0.33 part by weight or more and 1 part by weight or less of the ethylenically unsaturated crosslinking agent. When the content of the ethylenically unsaturated crosslinking is excessively reduced to less than 0.033 parts based on 1 part by weight of the styrene monomer, the crosslinking density of the polystyrene-based polymer is reduced, and thereby it becomes difficult for the particle morphology to stably maintain a spherical shape, and there is a limitation in that it is difficult to lower the overall density of the polystyrene-based particles to a target level.

On the other hand, when the content of the ethylenically unsaturated crosslinking agent is excessively increased to 3 parts by weight or more based on 1 part by weight of the styrene monomer, there is a limitation in that it is difficult for the particle morphology to stably maintain a spherical shape.

Examples of the ethylenically unsaturated crosslinking agent may include divinylbenzene.

Based on the total surface area of the polystyrene-based particles, the ratio of the surface area of the polystyrene-based particles in contact with the micropores existing on the surface of the polystyrene-based particles may be less than 0.01%. The total surface area of the polystyrene-based particles means the sum of the surface areas exposed in air at the outermost of the polystyrene-based particles, and the surface area of the polystyrene-based particles in contact with the micropores existing on the surface of the polystyrene-based particles means the sum of the surface areas in which the micropores existing on the polystyrene-based particle surface are in contact with the outermost surface of the polystyrene-based particles. Further, the micropore is a pore having a maximum diameter of a micrometer size, for example, means a pore having a maximum diameter of 1 μm or more and 500 μm or less.

More specifically, based on the total surface area of the polystyrene-based particles, the ratio of the surface area of the polystyrene-based particles in contact with the micropores existing on the surface of the polystyrene-based particles can be calculated according to the following Equation 3.

Based on the total surface area of the polystyrene-based particles, the ratio (%) of the surface area of the polystyrene-based particles in contact with the micropores existing on the surface of the polystyrene-based particles=[(Surface area of the polystyrene-based particles in contact with micropores existing on the surface of the polystyrene-based particles)/(Total surface area of the polystyrene-based particles)]*100 [Equation 3]

"Based on the total surface area of the polystyrene-based particles, the ratio of the surface area of the polystyrene-based particles in contact with the micropores existing on the surface of the polystyrene-based particles is less than 0.01%" means that there are no micro-sized pores existing on the surface of the polystyrene-based particles, or there are very few micro-pores to the extent that it can be seen to be almost nonexistent.

Conventionally, in order to reduce the density of polystyrene particles, a foaming agent has been added to produce foamed styrene, but in this case, the distribution of the diameter range and density range of the polystyrene particles becomes too broad and thereby, it was difficult to secure a yield within a range applicable as a microcarrier for cell culture.

On the other hand, based on the total surface area of the polystyrene-based particles, the polystyrene-based particles in contact with the micropores existing on the surface of the polystyrene-based particles have a surface area ratio of less than 0.01%, and therefore, unlike the conventional foamed styrene, the foaming process using a foaming agent does not proceed at all, so there is an advantage in that the distribution of the diameter range and the density range of the polystyrene particles can be more precisely adjusted.

The polystyrene-based particles may have an average diameter of 50 μm or more and 400 μm or less, or 60 μm or more and 390 μm or less. When the average diameter of the polystyrene-based particles satisfies the above-mentioned range, it is excellent in cell adhesion and culture performance. Meanwhile, when the average diameter of the polystyrene-based particles is less than 50 μm, the surface area where cell culture is possible is small, which may cause problems that culture efficiency is reduced. When the average diameter of the polystyrene-based particles is more than 400 μm, there may be problems that interaction between adherent cells is lowered, the cell density in an incubator is reduced, and the cell culture efficiency is deteriorated.

The diameter of the polystyrene-based particles means the distance between two points where a straight line passing through the center of gravity of the polystyrene-based particles meets the outermost surface of the polystyrene-based particles. The average diameter of the polystyrene-based particles may be calculated by confirming the diameters of all polystyrene-based particles contained in the microcarrier for cell culture through an optical microscope. Further, the average particle diameter of the polystyrene-based particles can also be confirmed through the diameter of all polystyrene-based particles obtained in the production process of the polystyrene-based particles or their average diameter.

The polystyrene-based particles may be a group of individual particles having an average diameter of 50 μm or more and 400 μm or less, or 60 μm or more and 390 μm or less, and individual particles contained in such group may have an average diameter of 50 μm or more and 400 μm or less, or 60 μm or more and 390 μm or less. More specifically, 95%, or 99% of the individual particles contained in the group may have a diameter of 50 μm or more and 400 μm or less, or 60 μm or more and 390 μm or less.

A primer polymer layer, a cell adhesion inducing layer, or a combination layer thereof may be further contained on the surface of the polystyrene-based particles. That is, one type of primer polymer layer, one type of cell adhesion inducing layer, or a mixed layer of one type of primer polymer layer and one type of cell adhesion inducing layer may be further contained on the surface of the polystyrene-based particles. In the mixed layer of one type of primer polymer layer and one type of cell adhesion inducing layer, the laminating order thereof is not particularly limited. Both a structure in which a cell adhesion inducing layer is laminated on a primer polymer layer and a structure in which a primer polymer layer is laminated on a cell adhesion inducing layer is applicable.

On the other hand, the primer polymer layer serves as an adhesive layer capable of introducing a functional polymer onto the surface of polystyrene-based particles without a functional group, so that a polymer layer for cell attachment is effectively introduced onto the surface of the microcarrier, and it can be stably maintained even during culture.

Examples of the primer polymer layer are not particularly limited, but catechol derivatives capable of inducing aqueous phase adhesion may include any one or more selected from the group consisting of L-dihydroxyphenylalanine (L-DOPA), dopamine, polydopamine, norepinephrine, epinephrine, epigallocatechin and its derivatives.

On the other hand, the cell adhesion inducing layer is composed of a cell adhesion substance, which serves to provide a site where the cell transmembrane proteins can bind, and allows adherent cells to stably attach, spread, and culture.

Examples of the polymer forming the cell adhesion inducing layer are not particularly limited, and may include any one or more selected from the group consisting of gelatin, collagen, fibronectin, chitosan, polydopamine, poly L-lysine, vitronectin, peptides including RGD, acrylic polymers including RGD, lignin, cationic dextran and derivatives thereof.

As one example, the microcarrier includes a primer polymer layer formed on the surface of the polystyrene-based particles, and they are dispersed in water by modifying the surface of the microcarrier to be hydrophilic, and a cell adhesion inducing layer is introduced on the surface of the primer polymer layer, so that the degree of floating of the microcarrier in the culture medium can be adjusted, and cells are stably adhered and cultured.

On the other hand, the ratio between the radius of the polystyrene-based particles and the thickness of the primer polymer layer may be 1:0.00001 to 1:0.01, or 1:0.0001 to 1:0.001.

When the ratio between the radius of the polystyrene-based particles and the thickness of the surface coating layer is less than 1:0.00001, the primer polymer layer is too thin compared to the polystyrene-based particles and thus, the effect of modifying the surface of the microcarrier to be hydrophilic is insignificant. If the ratio exceeds 1:0.01, the polymer layer of the primer becomes thicker compared to the polystyrene-based particles, which may reduce the degree of adhesion between cells and microcarriers during cell culture.

On the other hand, the microcarrier for cell culture has a perfect spherical particle ratio of more than 90% and 100% or less, or 92% or more and 100% or less, or 95% or more and 100% or less, or 96% or more and 99% or less without damage and breakage according to the following Equation 1.

Ratio of perfect spherical particles without damage and breakage (%)=(Number of polystyrene-based particles with perfect spherical shape without damage and breakage)/Total number of polystyrene-based particles)×100. [Equation 1]

The ratio of perfect spherical particles without damage and breakage according to Equation 1 can be obtained by measuring, through SEM, the number of particles having a perfect spherical shape without damage and breakage among the total particles for the microcarrier for cell culture of the one embodiment, and calculating the percentage ratio of the number of perfect spherical particles without damage or breakage to the total particles.

That is, the microcarrier for cell culture may contain a plurality of polystyrene-based particles, and among such a plurality of polystyrene-based particles, whether or not they have a completely spherical shape without damage or destruction can be visually determined through SEM.

When the ratio of perfect spherical particles is reduced to 90% or less without damage and breakage according to Equation 1, the surface of the particles is not uniform and the number of recessed atypical particles increases, and the atypical particles float in the cell culture medium and apply a physical impact to the cells being cultured, thereby deteriorating the cell culture efficiency to the extent that cell culture is impossible.

Further, the microcarrier for cell culture has a porosity of 0% or more and less than 8%, or 1% or more and less than 8%, or 2% or more and less than 8%, or 3% or more and less than 8%, or 3.9% or more and 7.5% or less, or 6.5% or more and 7.5% or less according to the following Equation 2.

Porosity (%)=[1−(Apparent density of polystyrene-based particles/True density of polystyrene-based particles)]×100. [Equation 2]

The apparent density is a density obtained using the actual particle volume including the pores between particles, and the true density is the density obtained by using the volume of only the particle materials excluding the pores.

In the porosity according to Equation 2, the apparent density of polystyrene-based particles can be measured by adding them to an aqueous ethanol solution having a density of 0.95 g/cm$^3$ and water having a density of 1 g/cm$^3$, respectively, and checking whether the particles are floated or sedimented, and the true density can be measured using He pycnometry.

"The porosity according to Equation 2 is 0" means that the hydrocarbon oil does not phase-separate in the polymerization process and disappears during polymerization, so that the polystyrene-based particles do not contain one hydrocarbon oil having 12 or more carbon atoms. Further, "the porosity according to Equation 2 is more than 0% and less than 8%" means a state in which the hydrocarbon oil is phase-separated in the polymerization process and then disappears or partially remains in the polymerization and washing process, so that the polystyrene-based particles contain both hydrocarbon oil having 12 or more carbon atoms and pores derived from hydrocarbon oil having 12 or more carbon atoms.

When the porosity according to Equation 2 is excessively increased to 8% or more, the density of the polystyrene-based particles is excessively reduced, and microcarriers float only on the surface of the culture medium at early stage of culture, which may cause a problem in that it is difficult to attach cells.

2. Method for Producing Microcarriers for Cell Culture

According to another embodiment of the present disclosure, there can be provided a method for producing a microcarrier for cell culture, which comprises the step of proceeding a suspension polymerization reaction of a monomer composition containing a styrene monomer in the presence of a hydrocarbon oil having 12 or more carbon atoms.

The details concerning the hydrocarbon oil and the styrene monomer include all the contents described above in the one embodiment.

The monomer composition may be a mixture of 1 part by weight of the styrene monomer and more than 0.033 parts by weight and less than 3 parts by weight of the ethylenically unsaturated crosslinking agent. Specifically, when the content of the ethylenically unsaturated crosslinking agent is excessively reduced to less than 0.033 parts by weight based on 1 part by weight of the styrene monomer, the crosslinking density of the polystyrene-based polymer decreases and thereby, it is difficult to stably produce pores generated by hydrocarbon oil, and it is difficult to sufficiently reduce the density of the polystyrene-based particles. Further, there is a limitation in that it is difficult for the particle morphology to maintain a perfect spherical shape without damage or breakage.

On the other hand, when the content of the ethylenically unsaturated crosslinking agent is excessively increased to 3 parts by weight or more based on 1 part by weight of the styrene monomer, there is a limitation in that the overall density of the polystyrene-based particles does not easily decrease to the desired level while the crosslink density of the polystyrene-based polymer increases.

Further, based on the weight of the monomer composition, the content of the hydrocarbon oil may be 10% by weight or more and 30% by weight or less, or 14% by weight or more and 20% by weight or less. When the content of the hydrocarbon oil is excessively reduced, the amount of the hydrocarbon oil phase-separated during polymerization is small and thus, it is difficult to sufficiently reduce the density of the polystyrene-based particles. Further, when the content of the hydrocarbon oil is excessively increased, it becomes difficult for the polystyrene-based particles to have a spherical shape, and the uniformity of the produced particles is reduced.

More specifically, the suspension polymerization reaction of the monomer composition may include a step of mixing the monomer composition with an aqueous dispersion and applying a shear force to homogenize the monomer composition in the aqueous dispersion in the form of droplets; and a step of suspension-polymerizing the homogenized monomer composition at a stirring speed of 300 rpm or more and 1000 rpm or less.

In the step of suspension-polymerizing the homogenized monomer composition at a stirring speed of 300 rpm or more and 1000 rpm or less, or 400 rpm or more and 800 rpm or less, it is possible to produce a microcarrier for cell culture that can reduce the density of microcarriers for cell culture and has high ratio of perfect spherical particles without damage and destruction, while internal pores are formed by phase separation of polystyrene and hydrocarbon oil during the formation of the particle structure of polystyrene and hydrocarbon oil.

In the step of suspension-polymerizing the homogenized monomer composition at a stirring speed of 300 rpm or more and 1000 rpm or less, or 400 rpm or more and 800 rpm or less, examples of the suspension polymerization conditions are not particularly limited, but for example, the suspension polymerization can be performed at a temperature of 50° C. or more and 100° C. or less for 3 hours or more and 18 hours or less.

On the other hand, the method for producing a microcarrier for cell culture may, after the step of proceeding the suspension polymerization reaction, include a step of washing the suspension-polymerized reaction product and a step of drying it.

Specifically, the step of washing the suspension-polymerized reaction product may include a step of filtering the suspension-polymerized reaction product through a sieve of 50 μm or more and 100 μm or less, followed by stirring in 100% ethanol 5-7 times at room temperature.

The step of drying the suspension-polymerized reaction product includes a step of placing in a vacuum oven and vacuum drying at room temperature. However, the present disclosure is not limited thereto, and a drying method known to be commonly used can be used without particular limitation.

On the other hand, the method for producing the microcarrier for cell culture of the other embodiment may, after the step of proceeding the suspension polymerization reaction, further include a step of applying a primer polymer layer, a cell adhesion inducing layer, or a combination layer thereof onto the surface of the suspension-polymerized reaction product.

The details concerning the primer polymer layer and the cell adhesion inducing layer include all the contents described above in the one embodiment.

3. Cell Culture Composition

According to another embodiment of the present disclosure, there can be provided a cell culture composition comprising a cell and the microcarrier for cell culture of the one embodiment. The details concerning the microcarrier for cell culture includes all the contents described above in the one embodiment.

The cells are adherent animal cells, and examples thereof are not particularly limited. For example, the cells may be fibroblasts, epithelial cells, osteoblasts, chondrocytes, hepatocytes, human-derived umbilical cord blood cells, human bone marrow-derived mesenchymal stem cells, CHO (Chinese hamster ovary) cells, kidney cells (HEK293, BHK21, MDCK, vero cells, etc.), or a mixture of two or more thereof.

The density of the cells may be 1.02 g/cm$^3$ or more and less than 1.1 g/cm$^3$.

Further, a difference in density between the microcarrier for cell culture and the cells may be 0.02 g/cm$^3$ or more and 0.20 g/cm$^3$ or less. As the density difference between the cell culture microcarrier and the cell satisfies 0.02 g/cm$^3$ or more and 0.20 g/cm$^3$ or less, cells and microcarriers can be easily isolated through the difference in sedimentation rate due to gravity when isolating and recovering the microcarriers and cells after cell culture.

The cell culture composition may further include a medium solution. The medium solution may contain nutrients close to biological conditions based on body fluids such as plasma and lymph, and various additives for sufficiently satisfying environmental conditions such as pH, temperature, and osmotic pressure. This can use various substances widely known in the field of cell culture related technology without limitation.

In one example, the microcarrier for cell culture of one embodiment has a smaller density than the medium solution, is injected into the medium solution and floated in the medium solution under stirring conditions. Then, as the number of cells adhering to the surface of the low-density microcarriers increases, the density of the microcarriers to which the cells are attached (hereinafter, referred to as 'microcarrier-cell conjugate') gradually increases and gradually sinks into the medium solution.

Therefore, the microcarrier to which the cells are attached (microcarrier-cell conjugate) is treated by adding a cell removing enzyme, and then isolated through centrifugal separation, and the cells are isolated from the microcarrier-cell complex, and thus cultured cells can be easily secured.

Advantageous Effects

According to the present disclosure, a microcarrier for cell culture that can be isolated more easily at the time of isolating and recovering the microcarrier and cells after cell culture, while sufficiently securing the yield of microcarriers having a perfect spherical shape without damage and breakage, a method for producing the same, and a cell culture composition using the same can be provided.

BRIEF DESCRIPTION OF THE DRAWING

FIG. 1. shows an SEM image of the microcarrier for cell culture obtained in Example 1;

FIG. 2 shows an SEM image of the microcarrier for cell culture obtained in Reference Example 1;

FIG. 3 shows an SEM image of the microcarrier for cell culture obtained in Reference Example 5;

FIG. 4 is a SEM image showing the particle cross-sectional shape of the microcarrier for cell culture obtained in Example 2; and FIG. 5 is a SEM image showing the particle cross-sectional shape of the microcarrier for cell culture obtained in Comparative Example 1.

Hereinafter, the present disclosure will be described in more detail by way of examples. However, these examples are for illustrative purposes only, and the scope of the present disclosure is not limited thereby.

Example: Production of Microcarriers for Cell Culture

Example 1

2.5 g of polyvinyl alcohol was mixed with 250 g of water to prepare an aqueous dispersion, which was then stirred at room temperature for 20 minutes.

25 g of the total sum of styrene as a monomer, divinylbenzene as a crosslinking agent, and the oil as shown in Table 1 (charging amount: based on the total amount of oil added) were mixed at the content ratio shown in Table 1 below, and then was sufficiently dissolved. 2.06 wt. % of a benzoyl peroxide initiator (Sigma Aldrich) and 0.3125 wt. % of a tert-butyl peroxybenzoate initiator (Sigma Aldrich) were added to the mixture (charging amount of initiator: based on the total amount of monomer, crosslinking agent, and oil), and the mixture was further stirred for 5 minutes to prepare a monomer composition.

Then, the monomer composition was added to the aqueous dispersion, a shear force was applied to the aqueous dispersion and monomer composition at a speed of 800 rpm, and the monomer composition was dispersed in the form of fine droplets in an aqueous dispersion and allowed to homogenize.

The homogenized mixture was reacted under nitrogen purge at 90° C. for 6 hours while stirring at the stirring speed described in Table 1 below to prepare polystyrene particles, and the particles washed with ethanol were dried at room temperature and recovered.

After drying, the recovered particles were immersed in tris buffer (pH 8.0) in which dopamine hydrochloride was dissolved at 1 mg/mL, and coated under stirring at room temperature for 2 hours. The excess coating material was washed with ethanol, the particles were filtered on a 70 μm sieve, dried at room temperature, and the dried particles were used as a microcarrier for cell culture.

Examples 2 to 8

As shown in Table 1 below, a microcarrier for cell culture was prepared in the same manner as in Example 1, except that the weight ratio of styrene and divinylbenzene, oil, or agitation speed were used differently.

Comparative Example: Production of Microcarriers for Cell Culture

Comparative Examples 1 to 3

As shown in Table 1 below, a microcarrier for cell culture was produced in the same manner as in Example 1, except that the weight ratio of styrene and divinylbenzene, oil, and stirring speed were used differently.

Reference Example: Production of Microcarriers for Cell Culture

Reference Examples 1 to 8

As shown in Table 1 below, a microcarrier for cell culture was produced in the same manner as in Example 1, except that the weight ratio of styrene and divinylbenzene, and oil were used differently.

TABLE 1

| Suspension polymerization conditions | | | | | |
|---|---|---|---|---|---|
| Category | Weight ratio of styrene:divinyl benzene | Type of oil | Oil density | Amount of oil added | Stirring speed (rpm) |
| Example 1 | 1:0.33 | Isopar M | 0.791 | 14 | 800 |
| Example 2 | 1:0.33 | Isopar M | 0.791 | 20 | 800 |
| Example 3 | 1:0.33 | Isopar M | 0.791 | 20 | 400 |
| Example 4 | 1:1 | Isopar M | 0.791 | 20 | 800 |
| Example 5 | 1:0.33 | Dodecane | 0.750 | 14 | 800 |
| Example 6 | 1:0.33 | Dodecane | 0.750 | 20 | 800 |

TABLE 1-continued

| Suspension polymerization conditions | | | | | |
|---|---|---|---|---|---|
| Category | Weight ratio of styrene:divinyl benzene | Type of oil | Oil density | Amount of oil added | Stirring speed (rpm) |
| Example 7 | 1:0.33 | Hexadecane | 0.773 | 14 | 800 |
| Example 8 | 1:0.33 | Hexadecane | 0.773 | 20 | 800 |
| Comparative Example 1 | 1:0 | — | — | 0 | 800 |
| Comparative Example 2 | 1:0.33 | n-heptane | 0.684 | 14 | 800 |
| Comparative Example 3 | 1:0.33 | Iso-octane | 0.690 | 14 | 800 |
| Reference Example 1 | 1:0 | Isopar M | 0.791 | 20 | 800 |
| Reference Example 2 | 1:0 | Isopar M | 0.791 | 50 | 800 |
| Reference Example 3 | 1:0.0025 | Isopar M | 0.791 | 20 | 800 |
| Reference Example 4 | 1:0.033 | Isopar M | 0.791 | 20 | 800 |
| Reference Example 5 | 1:3 | Isopar M | 0.791 | 20 | 800 |
| Reference Example 6 | 1:0.33 | Isopar M | 0.791 | 7 | 800 |
| Reference Example 7 | 1:0.33 | Dodecane | 0.750 | 7 | 800 |
| Reference Example 8 | 1:0.33 | Hexadecane | 0.773 | 7 | 800 |

Experimental Example: Measurement of Physical Properties of Microcarriers for Cell Culture The physical properties of the cell culture microcarriers obtained in Examples and Comparative Examples were measured by the following method, and the results are shown in Table 2 below.

1. Particle Size

For the microcarriers for cell culture obtained in Examples and Comparative Examples, the diameters of 100 particles were measured through an optical microscope, and an arithmetic mean value thereof was calculated.

2. Apparent Density of Particles

For the microcarriers for cell culture obtained in Examples and Comparative Examples, a sample was prepared under the condition that the drying process has been completed. The sample was added to an ethanol aqueous solution having a density of 0.95 g/cm$^3$, 0.97 g/cm$^3$, 0.98 g/cm$^3$ or 0.995 g/cm$^3$, and a distilled water (DIW) having a density of 1 g/cm$^3$ under the conditions of room temperature (25° C.) and atmospheric pressure (1 atm). It was confirmed whether the particles are floated or sedimented, and the apparent density was evaluated according to the following criteria.

1) floated in an aqueous ethanol solution with a density of 0.95 g/cm$^3$: less than 0.95 g/cm$^3$ 2) sedimented in distilled water (DIW) with a density of 1 g/cm$^3$: more than 1 g/cm$^3$ 3) sedimented in ethanol aqueous solution with a density of 0.95 g/cm$^3$ and floated in distilled water (DIW) with a density of 1 g/cm$^3$: 0.95 g/cm$^3$ or more and less than 1 g/cm$^3$ 4) sedimented in an aqueous ethanol solution with a density of 0.95 g/cm$^3$ and floated in an aqueous ethanol solution with a density of 0.97 g/cm$^3$: 0.95 g/cm$^3$ or more and less than 0.97 g/cm$^3$ 5) sedimented in an aqueous ethanol solution with a density of 0.98 g/cm$^3$ and floated in an aqueous ethanol solution with a density of 0.995 g/cm$^3$: 0.98 g/cm$^3$ or more and less than 0.995 g/cm$^3$ 3. Ratio of Perfect Spherical Particles without Damage and Breakage Using the microcarriers for cell culture obtained in Examples and Comparative Examples, a sample was prepared under conditions in which the drying process has been completed, and the number of spherical particles (complete spherical particles not broken) among all particles in the sample was measured through SEM, and the number percent ratio of spherical particles was measured according to the following Equation 1.

Ratio of perfect spherical particles without damage and breakage (%)=(Number of particles with perfect spherical shape without damage and breakage/Number of total particles)×100. [Equation 1]

4. Internal Porosity of Particles

Using the microcarriers for cell culture obtained in Examples and Comparative Examples, a sample was prepared under conditions in which the drying process has been completed, and the true density was measured from the sample by He pycnometry, and the porosity was measured according to the following Equation 2.

Porosity (%)=[1−(Apparent density/True density)]×100 [Equation 2]

5. Particle Internal Structure and Pore Diameter (1) Particle Internal Structure For the microcarriers for cell culture obtained in Examples and Comparative Examples, the internal structure of particles was confirmed through SEM. Specifically, the particles were embedded in epoxy, and then subjected to milling to prepare a cross section, and then the shape of the particle cross section was confirmed through SEM.

(2) Pore Diameter

The particles were embedded in an epoxy, and subjected to ion milling to prepare a cross section, and then the shape of the particle cross section was confirmed with SEM to obtain the minimum and maximum diameters among the pores inside the particles.

6. Evaluation of the Recovery Efficiency of Microcarriers

The microcarriers for cell culture obtained in Examples and Comparative Examples were immersed in tris buffer (pH 8.0) in which dopamine hydrochloride was dissolved at 1 mg/mL, and coated for 2 hours at room temperature under stirring. The excess coating material was washed with ethanol, the particles were filtered through a 70 μm sieve and the dried at room temperature.

A culture medium containing mesenchymal stem cells (density: 1.05 g/cm$^3$) was filled in 100 mL vertical wheel bioreactor (PBS), and a polydopamine-coated microcarrier for cell culture was injected into the culture medium and stirred. After culturing at room temperature for 14 days, it was treated with 0.25% trypsin, then the culture solution was centrifuged, and the microcarriers floating in the supernatant were recovered. This was dried and then the weight was measured to evaluate the recovery efficiency.

7. Analysis of Pore Component

In order to analyze the components contained in the internal pores for the microcarriers for cell culture obtained in the Examples and Comparative Examples, the microcarriers for cell culture were freeze-pulverized and dissolved in chloroform to extract unreacted residual compounds. Detailed components were qualitatively and quantitatively analyzed through GC/FID (Gas Chromatography-flame ionization detector).

Specifically, a standard sample of styrene (1/4000 mg/mL~1 mg/mL), divinylbenzene (1/10000 mg/mL~1 mg/mL), Isopar M (1/400 mg/mL to 10 mg/mL) was prepared by concentration in a mixed solvent of chloroform and methanol in a 1:2 volume ratio. 1 uL of a standard sample was injected into a GC/FID instrument and a calibration curve was prepared. 1 uL of the unreacted residual compound solution extracted from the sample in Table 1 was injected, and the content was calculated using a calibration curve. For GC/FID measurement, a column on Rtx (styrene, Isopar M) or wax (divinylbenzene) with an inner diameter of 0.53 mm, a length of 30 m, and a film thickness of 5 μm was used. The initial oven temperature was started from 50° C. and the temperature was raised to 250° C. at a rate of 10° C./min. As the mobile phase gas, 15 mL/min of helium gas was used. At this time, it was marked as "0" if oil or a component derived therefrom was detected, and it was marked as "X" if oil or a component derived therefrom was not detected.

tions, and the recovery efficiency of the microcarriers after culture was also as high as 90%. On the other hand, the microcarrier for cell culture of Comparative Example 1 has a non-porous structure having no pores with an internal particle porosity of 0%, where the density increased to more than 1 g/cm$^3$, which caused a problem that the cells and microcarriers could not be isolated through centrifugal separation after cell culture and removal.

In addition, the microcarriers for cell culture of Comparative Examples 2 and 3 have an excessively low particle density of less than 0.95 g/cm$^3$, and under stirring conditions, the particles are suspended on the surface of the culture medium, and cell adhesion is reduced, so there was a problem that cell culture is not possible. Further, in the microcarriers for cell culture of Comparative Examples 2

TABLE 2

Experimental Example Measurement Results of Examples and Comparative Examples

| Category | Particle size (μm) | Apparent density of particles (g/cm$^3$) | Porosity (%) | Pore diameter (μm) | Ratio of perfect spherical particles without damage and breakage (%) | Particle internal structure | Recovery efficiency (%) | Analysis of pore components |
|---|---|---|---|---|---|---|---|---|
| Example 1 | 104(±24) | 0.98 or more 0.995 or less | 3.9 | Minimum: 1 Maximum: 4 | 99 (FIG. 1) | Porous | 90 | ○ |
| Example 2 | 92(±22) | 0.95 or more 0.97 or less | 7.1 | Minimum: 1 Maximum: 4 | 99 | Porous (FIG., 4) | 90 | ○ |
| Example 3 | 322(±51) | 0.95 or more 1 or less | 7.5 | Minimum: 1 Maximum: 4 | 99 | Porous | 90 | ○ |
| Example 4 | 99(±21) | 0.95 or more 1 or less | 6.7 | Minimum: 1 Maximum: 4 | 99 | Porous | 90 | ○ |
| Example 5 | 96(±30) | 0.95 or more 1 or less | 6.9 | Minimum: 1 Maximum: 4 | 99 | Porous | 90 | ○ |
| Example 6 | 105(±27) | 0.95 or more 1 or less | 7.3 | Minimum: 1 Maximum: 4 | 99 | Porous | 90 | ○ |
| Example 7 | 107(±23) | 0.95 or more 1 or less | 7.2 | Minimum: 1 Maximum: 4 | 99 | Porous | 90 | ○ |
| Example 8 | 102(±26) | 0.95 or more 1 or less | 6.5 | Minimum: 1 Maximum: 4 | 99 | Porous | 90 | ○ |
| Comparative Example 1 | 198(±99) | More than 1 | 0 | — | 100 | No pores (FIG. 5) | Cell-microcarriers can be separated by centrifugation | X |
| Comparative Example 2 | 93(±20) | 0.95 or less | — | Minimum: 1 Maximum: 4 | 90 | Porous | | ○ |
| Comparative Example 3 | 99(±15) | 0.95 or less | — | Minimum: 1 Maximum: 4 | 90 | Porous | Cell culture is not possible | ○ |
| Reference Example 1 | 92(±66) | Greater than 1 | — | Minimum: 1 Maximum: 4 | 0 (FIG. 2) | Porous | Cell culture is not possible | ○ |
| Reference Example 2 | Particle production is not possible | — | — | — | — | — | Cell culture is not possible | — |
| Reference Example 3 | 80(±16) | More than 1 | — | Minimum: 1 Maximum: 4 | 50 | Porous | Cell culture is not possible | ○ |
| Reference Example 4 | 97(±24) | 0.95 or more 1 or less | — | Minimum: 1 Maximum: 4 | 50 | Porous | Cell culture is not possible | ○ |
| Reference Example 5 | 112(±22) | 0.95 or more 1 or less | — | Minimum: 1 Maximum: 4 | 70 (FIG. 3) | Porous | Cell culture is not possible | ○ |
| Reference Example 6 | 96(±26) | More than 1 | — | Minimum: 1 Maximum: 4 | 90 | Porous | Cell culture is not possible | ○ |
| Reference Example 7 | 120(±26) | More than 1 | — | Minimum: 1 Maximum: 4 | 90 | Porous | Cell culture is not possible | ○ |
| Reference Example 8 | 98(±24) | More than 1 | — | Minimum: 1 Maximum: 4 | 90 | Porous | Cell culture is not possible | ○ |

As shown in Table 2 above, the microcarriers for cell culture of Examples exhibit a porosity of 3.9% or more and 7.5% or less inside the particles, have a porous structure and satisfies a low density of 0.95 g/cm$^3$ or more and less than 1 g/cm$^3$, and at the same time, the ratio of perfect spherical particles without damage and breakage is 99% which is very high and thus, most of the particles could have homogeneously spherical shapes. In addition, it was confirmed that in the microcarriers for cell culture of Examples, carrier culture is effectively carried out under cell culture condiand 3, the ratio of perfect spherical particles without damage and breakage was measured to be 90%, and also the particle surface is not uniform and recessed particles are generated in a large amount compared to Examples, so that the cell culture efficiency is lowered to such an extent that the cell culture is not possible.

On the other hand, the microcarriers for cell culture of Reference Examples 1 to 5 have a perfect spherical particle ratio of 0% or more and 70% or less without damage or breakage, which is lower than Examples, and there is a limitation in that the shape of the particles is relatively non-uniform compared to Examples. Further, the microcarriers for cell culture of Reference Examples 6 to 8 have an apparent density of more than 1 g/cm$^3$ during cell culture, so that during culture, precipitation occurs during low-speed stirring, or the suspension of the culture solution is increased due to non-spherical particles. Thus, there was a problem in that cell culture efficiency is lowered to such an extent that cell culture is not possible due to physical impact in the future.

The invention claimed is:

1. A microcarrier for cell culture comprising: polystyrene-based particles containing at least one of hydrocarbon oil having at least 12 carbon atoms, or pores derived therefrom, wherein the polystyrene-based particles have an apparent density of 0.95 g/cm$^3$ or more and less than 1.00 g/cm$^3$.

2. The microcarrier for cell culture of claim 1, wherein:

a ratio of perfect spherical particles without damage and breakage according to the following Equation 1 is more than 90% and 100% or less:

Ratio of perfect spherical particles without damage and breakage (%)=(Number of polystyrene-based particles having a perfect spherical shape without damage and breakage/Number of entire polystyrene-based particles)×100. [Equation 1]

3. The microcarrier for cell culture of claim 1, wherein:

the polystyrene-based particles have a porosity of 0% or more and less than 8% according to the following Equation 2:

Porosity (%)=[1−(Apparent density of polystyrene-based particles/True density of polystyrene-based particles)]×100. [Equation 2]

4. The microcarrier for cell culture of claim 1, wherein:

the hydrocarbon oil has a density of 0.75 g/cm$^3$ or more and 0.80 g/cm$^3$ or less.

5. The microcarrier for cell culture of claim 1, wherein:

the hydrocarbon oil comprises a linear or branched saturated hydrocarbon compound having 12 or more and 50 or less carbon atoms.

6. The microcarrier for cell culture of claim 1, wherein:

the polystyrene-based particles comprise a polystyrene-based polymer in which the at least one of hydrocarbon oil having at least 12 carbon atoms, or pores derived therefrom are dispersed therein.

7. The microcarrier for cell culture of claim 6, wherein:

the polystyrene-based polymer comprises a reaction product of 1 part by weight of a styrene monomer; and more than 0.033 parts by weight and less than 3 parts by weight of an ethylenically unsaturated crosslinking agent.

8. The microcarrier for cell culture of claim 1, wherein:

the polystyrene-based particles have an average diameter of 50 μm or more and 400 μm or less.

9. The microcarrier for cell culture of claim 1, wherein:

the hydrocarbon oil is contained in an amount of 30% by weight or less based on the total weight of the polystyrene-based particles.

10. The microcarrier for cell culture of claim 1, wherein:

based on the total surface area of the polystyrene-based particles, a ratio of the surface area of the polystyrene-based particles in contact with micropores existing on the surface of the polystyrene-based particles is less than 0.01%.

11. The microcarrier for cell culture of claim 1, wherein:

the pores have a diameter of 0.1 μm to 5 μm.

12. The microcarrier for cell culture of claim 1, wherein:

a primer polymer layer, a cell adhesion inducing layer, or a combination thereof is further included on the surface of the polystyrene-based particles.

13. A method for producing a microcarrier for cell culture, comprising the step of proceeding a suspension polymerization reaction of a monomer composition containing a styrene monomer in the presence of hydrocarbon oil having at least 12 carbon atoms, wherein polystyrene-based particles are produced by the suspension polymerization in the presence of hydrocarbon oil and have an apparent density of 0.95 g/cm$^3$ or more and less than 1.00 g/cm$^3$.

14. The method of claim 13, wherein:

a content of the hydrocarbon oil is 10% by weight or more and 30% by weight or less based on the weight of the monomer composition.

15. The method of claim 13, wherein:

the monomer composition is a mixture of 1 part by weight of a styrene monomer and more than 0.033 parts by weight and less than 3 parts by weight of an ethylenically unsaturated crosslinking agent.

16. The method of claim 13, wherein:

the suspension polymerization reaction of the monomer composition comprises a step of mixing the monomer composition with an aqueous dispersion and applying a shearing force to homogenize the monomer composition in the aqueous dispersion in the form of droplets; and a step of suspension-polymerizing the homogenized monomer composition at a stirring speed of 300 rpm or more and 1000 rpm or less.

17. A cell culture composition comprising a cell and the microcarrier for cell culture of claim 1.

18. The cell culture composition of claim 17, wherein:

the cell comprises at least one compound selected from the group consisting of fibroblasts, epithelial cells, osteoblasts, chondrocytes, hepatocytes, umbilical cord blood cells, mesenchymal stem cells, CHO cells, and kidney cells.

19. The cell culture composition of claim 17, wherein:

a difference in apparent density between the microcarrier for cell culture and the cell is 0.02 g/cm$^3$ or more and 0.20 g/cm$^3$ or less.

* * * * *